United States Patent
Wu (10) Patent No.: US 8,571,636 B2
(45) Date of Patent: Oct. 29, 2013

(54) SHIELDED SURGICAL NAVIGATION SYSTEM THAT DETERMINES THE POSITION AND ORIENTATION OF THE TRACKED OBJECT WITH REAL AND VIRTUAL DIPOLES

(75) Inventor: Chunwu Wu, Texas Township, MI (US)

(73) Assignee: Stryker Corporation, Kalamazoo, MI (US)

( * ) Notice: Subject to any disclaimer, the term of this patent is extended or adjusted under 35 U.S.C. 154(b) by 1335 days.

(21) Appl. No.: 12/238,545

(22) Filed: Sep. 26, 2008

(65) Prior Publication Data
US 2009/0048509 A1    Feb. 19, 2009

Related U.S. Application Data

(63) Continuation of application No. PCT/US2007/064753, filed on Mar. 23, 2007.

(60) Provisional application No. 60/787,123, filed on Mar. 29, 2006.

(51) Int. Cl.
*A61B 5/05*    (2006.01)

(52) U.S. Cl.
USPC ........................................................ 600/424

(58) Field of Classification Search
USPC ................ 600/424, 407, 422, 410, 421, 423; 702/150, 152, 134, 95; 324/207.15, 324/207.17
See application file for complete search history.

(56) References Cited

U.S. PATENT DOCUMENTS

| | | |
|---|---|---|
| 4,287,809 A | 9/1981 | Egli et al. |
| 4,314,251 A | 2/1982 | Raab |
| 4,945,305 A | 7/1990 | Blood |
| 5,676,673 A | 10/1997 | Ferre et al. |
| 5,879,297 A | 3/1999 | Haynor et al. |
| 6,172,499 B1 | 1/2001 | Ashe |
| 6,201,987 B1 * | 3/2001 | Dumoulin ..................... 600/424 |
| 6,636,757 B1 * | 10/2003 | Jascob et al. .................. 600/424 |
| 6,774,624 B2 * | 8/2004 | Anderson et al. ........ 324/207.17 |
| 6,993,443 B2 * | 1/2006 | Harle .............................. 702/95 |
| 7,096,148 B2 * | 8/2006 | Anderson et al. ............. 702/134 |

(Continued)

FOREIGN PATENT DOCUMENTS

| | | |
|---|---|---|
| WO | 0133231 A2 | 5/2001 |
| WO | 02098273 A2 | 12/2002 |

OTHER PUBLICATIONS

EPO ISA Search Report and Written Opinion for PCT App. No. PCT/US2007/064753, Sep. 2007.

*Primary Examiner* — Long V. Le
*Assistant Examiner* — Lawrence Laryea (57) ABSTRACT

A system for determining the position and orientation of a tracked object by measuring electromagnetic energy. The system includes a shield of magnetic permeable material positioned on one side of the object to be tracked. A transmitter emits the electromagnetic energy and there is a tracker sensor. One of the transmitter or tracker sensor is attached to the object to be tracked. A correction sensor is at fixed location relative to the transmitter assembly. Both sensors assemblies measure the electromagnetic energy emitted by the transmitter. Based on the energy measured by the correction sensor, the location of a virtual dipole that mirrors the transmitter, the real dipole, on the opposite side of the shield is determined. Based on the positions of the real and virtual dipoles and the energy measured by the tracker sensor, the position and orientation of the tracker sensor relative to the transmitter is determined.

18 Claims, 7 Drawing Sheets

(56) References Cited

U.S. PATENT DOCUMENTS

| | | | |
|---|---|---|---|
| 7,542,869 B2 * | 6/2009 | Gandelsman et al. | 702/152 |
| 7,835,779 B2 * | 11/2010 | Anderson et al. | 600/407 |
| 8,290,572 B2 * | 10/2012 | Martinelli et al. | 600/424 |
| 2003/0216639 A1 | 11/2003 | Gilboa et al. | |
| 2005/0165297 A1 | 7/2005 | Anderson et al. | |
| 2006/0252987 A1 | 11/2006 | Hasegawa et al. | |
| 2006/0264732 A1 | 11/2006 | Wu | |
| 2007/0078334 A1 * | 4/2007 | Scully et al. | 600/424 |
| 2008/0287771 A1 * | 11/2008 | Anderson | 600/410 |

* cited by examiner

SHIELDED SURGICAL NAVIGATION SYSTEM THAT DETERMINES THE POSITION AND ORIENTATION OF THE TRACKED OBJECT WITH REAL AND VIRTUAL DIPOLES

RELATIONSHIP TO EARLIER FILED APPLICATIONS

This application is a continuation of PCT Application No. PCT/US2007/064753 filed 23 Mar. 2007 which claims priority from U.S. Provisional Patent Application No. 60/787,123 filed 29 Mar. 2009. The contents of the priority applications are explicitly incorporated herein by reference.

FIELD OF THE INVENTION

This invention is generally related to a system and method for determining the location of an object, such as the location of an object in a surgical field. More specifically, this invention is related to a system and method for determining the location of an object using electromagnetic radiation wherein a shield blocks the effects of a metal object that may be present.

BACKGROUND OF THE INVENTION

There are number of fields of human endeavor wherein it is useful, if not necessary, to know precisely the location and orientation of an object within a space. Surgery is one such field in which this information is desirable. Surgical navigation systems are available that enable medical personnel to know, with a high degree of precession, the location and orientation of surgical instrument or implant relative to a surgical site on the patient. Often this information is used in surgical procedures to facilitate the accurate removal and shaping of tissue. In an orthopedic surgical procedure, the information provided by the surgical navigation system ensures that an implant is precisely positioned.

Surgical navigation systems and other position-locating systems use different means to identify the locations and orientations of the objects they track. A number of commercially available surgical navigation systems rely on light tracking to determine the position of the tracked object. Some systems include trackers that are attached to the objects being tracked. Each tracker emits a number of light beams. Often light is emitted in the infrared wavelengths. A static device, referred to as a localizer, has light sensitive-receivers. Based on the locations from which the individual light beams are received at a localizer, a processor, also part of the system, determines both the position and orientation of the tracker. Based on this information, the position and orientation of the device attached to the tracker is inferentially determined.

Often, at the start of a medical procedure, the position of the patient's body tissue is mapped into a memory integral with the processor. Based on these data and the inferential determination of the tracked object, the surgical navigation system presents an image on a display that indicates the position of the tracked object relative to the body tissue. This allows a surgeon to virtually "view" the position of the object that is otherwise be concealed by overlying tissue.

In an orthopedic surgical procedure, a surgical navigation system is also used to measure the range of motion of the body limb(s) subject to the procedure. These measurement data facilitate the fitting of the implant to the patient to increase the likelihood of successful outcome of the procedure.

Light-based surgical navigation systems work reasonably well for providing object location and orientation data in a surgical setting. Nevertheless, there is a drawback associated with these systems. A light-based navigation system requires a line-of-sight between the light emitting components and the light-sensitive localizer. If the line is broken, the ability of the system to provide object position and location data may be interrupted. Thus, medical personnel using such system must make a concerted effort to keep their own body parts as well as other surgical devices from entering into the space wherein such lines-of-sight may be present.

If the breaking of a line-of-sight results in the interruption of the generation of the object position and location data, it may be necessary stop the procedure until the system can again provide the data. Such delays reduce the overall efficiency of the surgeon performing the procedure. Moreover, such delays can increase the overall length of time it takes to perform the procedure. This is counter to an objective of modern surgical practice, to perform the procedure as quickly as possible. Surgeons work to this goal to reduce the amount of time the patient is held under anesthesia and his/her body is exposed and open to infection.

Recently, there have been efforts to employ electromagnetic field-sensing systems as surgical navigation systems. Generally, this type of navigation system includes one or more transmitters that emit electromagnetic energy. There is a sensor assembly with one or more transducers that are sensitive to electromagnetic energy. To provide both position and location information about an object, it is typically necessary to transmit plural fields and monitor the strength of each signal at plural antennae. Some of these transmitters emit electromagnetic energy upon being energized by AC drive signals. Others of these transmitters emit electromagnetic energy upon being energized by DC pulse signals. Based on the strength of the electromagnetic fields measured by the sensor, a processor determines the position and orientation of the sensor relative to the transmitter.

An electromagnetic navigation system does not require a line-of-sight path between the transmitter and sensor. A surgeon could allow his/her arm to enter the space between the system's transmitter and sensor without being concern that such action will result in the interruption of the generation of the object position and orientation-defining data.

Nevertheless, care must be taken when using an electromagnetic navigation system, especially in a surgical setting. This is because metal objects exposed to electromagnetic waves from a first source, in turn, generate their own electromagnetic waves. When ferrous metals, such as cold rolled steel, are exposed to magnetic waves, the metal itself becomes magnetized. The metal, in turn, generates its own magnetic fields. This added magnetic field is sensed by the sensor. This added magnetic field thus introduces an error into the magnetic field measurements made by the sensor.

One proposed means to reduce the adverse affects ferrous metals have on a surgical navigation system is to provide shielding around the surgical site. This shielding is positioned between the space in which the components of the surgical navigation system are located and the space into which the metal objects may be introduced. The shield blocks the transmission of the electromagnetic waves. Thus, metal objects that are separated by the shield neither become magnetized nor generate their own magnetic fields that can affect the measurements made by the navigation system sensor.

One proposed shielded magnetic field surgical navigation system includes an operating room table to which a metal plate formed from material with a high magnetic permeability is mounted. The system transmitter is mounted to the table at a fixed relationship to the metal plate. The plate blocks the adverse affects that would otherwise be introduced by the presence of ferromagnetic objects located on the side of the plate opposite the shield.

In the above system, the highly magnetic permeable plate itself is a source of interference. However, because the transmitter and plate are at fixed relationship relative to their relative position and orientation, this interference can be calculated at system assembly. The processor used to convert the sensor data to data that accurately indicates position, based on the known interference data, factors out the affect of this interference.

A clear limitation of the above-described system is that it requires the transmitter to remain at a fixed location relative to the shielding plate. This means the shielding could not be used with a system with a moving transmitter. An advantage of providing a moving transmitter is that it allows the transmitter to be placed relatively close to the sensor the position of which is being tracked. This relatively close positioning makes its possible to transmit relatively low power signals to the sensor will still ensuring the sensor is able to generate signals that, with a high degree of accuracy, can be used to determine its position and orientation.

Moreover, the proposed system is understood to require the placement of the transmitter relatively close to the shield, 10 cm or less. This is believed to require the retrofitting of existing operating room beds (tables) to facilitate the close placement of the transmitter and shield or the instillation of an operating room table especially designed to accommodate these components.

SUMMARY OF THE INVENTION

This invention is directed to a new and useful system and method for determining the position and orientation of an object by using magnetic field sensing. The system of this invention includes a shield that isolates the navigation transmitter and sensor from nearby ferromagnetic objects that could adversely affect the tracking of the sensed object. The system and method of this invention are further designed to allow both the transmitter and sensor to be moved relative to the shield.

Further, the system of this invention is designed so the transmitter can be spaced a relatively large distance away from the shield, 0.5 meters or more. Thus, the system of this invention is designed to be relatively easily integrated into use with an existing operating room table.

The system and method of this invention is based on the principal that, in an environment in which a shield is present, for every real electromagnetic dipole, transmitting element, present one side of the shield, a virtual dipole can be considered to be present on the opposite side.

Accordingly, the system of this invention includes a transmitter assembly, a tracker sensor assembly and a correction sensor assembly. The transmitter assembly and the tracker sensor assembly are arranged so that one of these assemblies is able to move relative to the other of these assemblies. Often, but not always, the transmitter assembly is fitted to a relatively static localizer. The tracker sensor assembly is attached to the moving object, the position and orientation of which is to be tracked. The correction sensor assembly is fixedly mounted to the transmitter assembly so as to be at a fixed position and orientation relative to the transmitter assembly.

In the system of this invention all three assemblies, the transmitter assembly, the tracker sensor assembly and the correction sensor assembly, can be moved relative to the shield.

In the method of this invention, measurements of the electromagnetic (EM) fields emitted by the transmitter assembly are measured by both sensor assemblies. The EM signals measured by the correction sensor assembly are based on the proximity of the transmitter and correction sensor assemblies to the shield. Based on these signals, the position of the virtual dipole is calculated.

In the shielded environment, the signals received by the tracking sensor are based on those emitted by both the real and virtual dipoles. The position and orientations of the real dipoles can be considered to be the reference origin and orientation of the space in which is occurring. The position and orientation of the virtual dipoles relative to this reference position and orientation is known due to the above-described processor. The position of the virtual is known from conventional tracking methods. Since the positions of the real and virtual dipoles are known, these data are used to determine the position of the tracking sensor.

The system of this invention allows the transmitter assembly to be moved relative to shield. Further this invention is constructed so that the transmitter can be placed relatively large distance away from the shield. Thus, use of this system in an operating room does not require installation of either a custom designed operating room table or the extensive reconfiguration of an existing operating room table.

BRIEF DESCRIPTION OF THE DRAWINGS

This invention is pointed out with particularity in the associated claims. The above and other features and benefits of this invention are understood by the following Detailed Description taken in conjunction with the accompanying drawings in which:

DETAILED DESCRIPTION

I. Theoretical Foundation of Shield Effect

Figure 1:
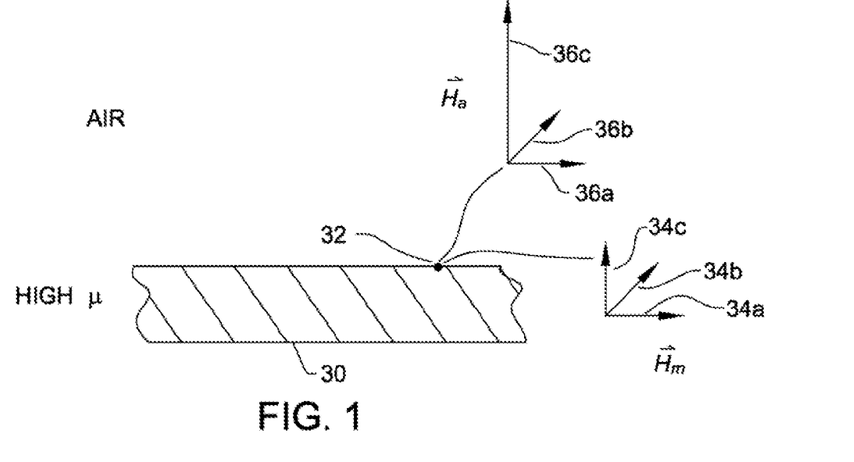
FIG. 1 is a diagrammatic representation of the relative strengths of the parallel and normal components of a magnetic field on the opposed sides of a shield-air interface.

The system and method of this invention is understood by appreciating electromagnetic fields in the vicinity of a shield, a component having a high magnetic permeability, μ. FIG. 1 illustrates this environment. Here a shield 30 is formed from a metal having a high magnetic permeability such as steel. At the surface of shield 30, the boundary between the shield and the ambient environment, there is no current flow. Accordingly, at a point 32 at this interface:

$$(\vec{B}_S - \vec{B}_A) \cdot \vec{n} = 0 \quad (1)$$

and $$(\vec{H}_S - \vec{H}_A) \times \vec{n} = 0 \quad (2)$$

Here, $\vec{B}_S$ and $\vec{B}_A$ are, respectively, the magnetic induction, flux density, of the shield 30 and air, respectively, at boundary point 32. Variables $\vec{H}_S$ and $\vec{H}_A$ are the strength of the magnetic field of, respectively, the shield and the air at the interface. Vector $\vec{n}$ is the vector normal to the interface between shield 30 and the air. The relationship between magnetic induction and flux density is:

$$\vec{B} = \mu \vec{H} \quad (3)$$

Accordingly, substituting Equation (3) in Equation (1) and rearranging Equations (1) and (2) above, the following magnetic field relationships are apparent at the boundary point:

$$\vec{H}_A \cdot \vec{n} = \frac{\mu_S}{\mu_A} \vec{H}_S \cdot \vec{n} \quad (4)$$

and $$\vec{H}_A \times \vec{n} = \vec{H}_S \times \vec{n} \quad (5)$$

Typically, material forming shield 30 is considered highly permeable, $\mu_s/\mu_a$ is $10^4$ or higher. This fact and Equations 4 and 5 collectively indicate two relationships between the magnetic fields of the shield 30 and the adjacent air layer. First, that the parallel components of the magnetic field for the shield and air are equal. Secondly, that the normal component of the magnetic field in the air at the boundary is much higher than the normal component of the field in the shield. Thus, at the boundary, the magnetic field in the air is perpendicular to the surface of the shield 30.

This is represented in FIG. 1 by the relative lengths of arrows 34a, 34b and 34c and arrows 36a, 36b and 36c. Arrows 34a and 34b are arrows representative of magnetic field strength in the plane of the shield 32 on the shield side of interface point 32. Arrows 36a and 36b are arrows representative of magnetic field strength in the plane of the air along the air side of the interface at point 32. Given the above discussed relationships, arrows 34a, 34b, 36a and 36b are substantially equal. Arrow 34c is representative of magnetic field strength at the interface of the shield 30, point 32 perpendicular to the interface. Arrow 36c is representative of the magnetic field strength at the interface in the air. Given the above discussed relationships, that the magnetic field in the air normal to the boundary is larger than the corresponding field in the shield, arrow 36c is significantly longer than arrow 34c.

The above relationships thus means that, at the interface between the shield 30 and the air, the magnetic field "bends" to become normal to the interface.

Since the magnetic field at the shield-air boundary is perpendicular to the boundary, this means that a dipole, a navigation transmitter, spaced from the shield can be represented by a virtual dipole on the opposed side of the shield. This principal is understood by FIG. 2 wherein a dipole 40 is shown perpendicular to line 44.

Figure 2:
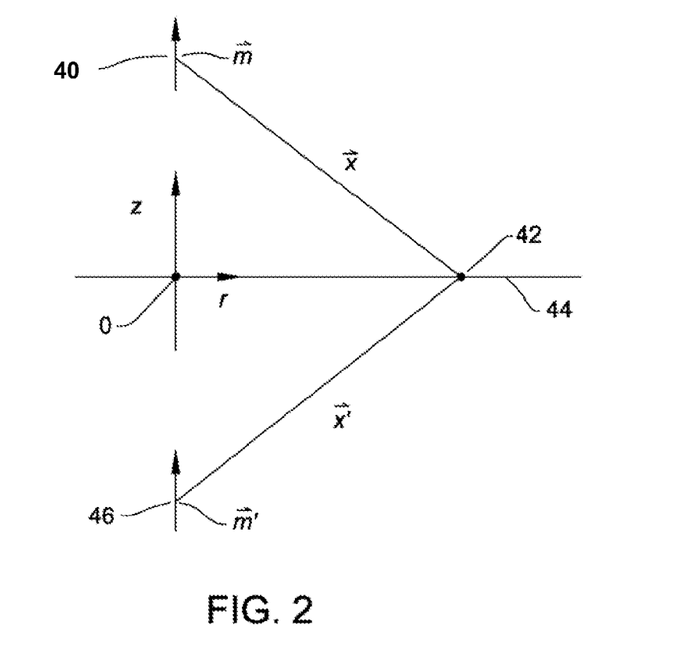
FIG. 2 is a diagrammatic representation of device that emits electromagnetic energy, a real dipole, normal to the shield-air interface and the virtual dipole formed by the shield.

Assuming a shield is not present, in an air environment, then at a point 42 along line 44, the magnetic field is:

$$\vec{H}_A = \vec{B}_A = \frac{3\hat{x}(\hat{x} \cdot \vec{m}) - \vec{m}}{|\vec{x}|^3} \quad (6)$$

Here, $\vec{m}$ is the magnitude and direction of dipole 40. Vectors $\vec{x}$ and $\hat{x}$ are, respectively, the vector and its unit vector from dipole 40 to point 42.

For a Gaussian unit system, the permeability of air is 1. In the situation of FIG. 2, the r axis is the horizontal distance from origin O and the z axis is the vertical distance from origin O. Dipole 40 is centered over the origin. In this system $\hat{e}_r$ and $\hat{e}_z$ are, respectively, the unit vectors along the r and z axes. Therefore, $$\vec{m} = m \hat{e}_z \quad (7)$$

and $$\hat{x} = r \hat{e}_r + z \hat{e}_z \quad (8)$$

In Equation 8, r and z are projections of unit vector $\hat{x}$ on the r and z axes, respectively.

Substituting Equations 7 and 8 into Equation 6 yields the following relationship:

$$\vec{H}_A = \frac{3\hat{x}(\hat{x} \cdot \vec{m}) - \vec{m}}{|\vec{x}|^3} \quad \text{(Equation 6)}$$

$$= \frac{m}{|\vec{x}|^3}(3(r\hat{e}_r + z\hat{e}_z)z - \hat{e}_z) \quad (9a)$$

$$= \frac{m}{|\vec{x}|^3} 3zr\hat{e}_r + \frac{m}{|\vec{x}|^3}(3z^2 - 1)\hat{e}_z \quad (9b)$$

According to Equation 9b, the normal component of the magnetic field at point 42 in air is $$\frac{m}{|\vec{x}|^3}(3z^2 - 1)$$

and the parallel component is $$\frac{m}{|\vec{x}|^3} 3zr.$$

If a shield, represented by line 44, is present at point 42, the characteristics of magnetic field $\vec{H}_A$ present at the point changes. This is because, as discussed above with respect to Equations 4 and 5, the field becomes totally perpendicular to the boundary line. The parallel component of the field can be considered to go to zero.

This means that the parallel component of the field, $$\frac{m}{|\vec{x}|^3} 3zr,$$

is canceled out by another field. The system and method of this invention assume that this parallel component of the field is canceled out by a virtual dipole 46. Virtual dipole 46, it is observed, is located at the mirror image position of dipole 40 on the opposite side of shield 30 and oriented in the same direction. In FIG. 2 vector $\vec{x}'$ and vector $\hat{x}'$ are, respectively, the vector and unit vector from virtual dipole 46 to point 42. Vector $\vec{m}'$ is the magnitude and direction of the virtual dipole 46. Accordingly, the following equations define the virtual dipole 46, its unit vector to point 42 and the length of vector $\vec{x}'$:

$$\vec{m}'=\vec{m}=m\hat{e}_z \quad (10)$$

$$\hat{x}'=r\hat{e}_r-z\hat{e}_z \quad (11)$$

and $$|\vec{x}'|=|\vec{x}| \quad (12)$$

The magnetic field virtual dipole 46 produced at point 42 is determined as follows:

$$\vec{H}'_A = \frac{3\hat{x}'(\hat{x}'\cdot\vec{m}')-\vec{m}'}{|\vec{x}'|^3} \quad \text{(From Equation 6)}$$

Then, substituting for $\vec{m}'$, $\hat{x}'$, and $|\vec{x}'|$ from Equations 10, 11 and 12:

$$= \frac{m}{|\vec{x}|^3}(3(r\hat{e}_r-z\hat{e}_z)(-z)-\hat{e}_z) \quad (13a)$$

$$= -\frac{m}{|\vec{x}|^3}3zr\hat{e}_r + \frac{m}{|\vec{x}|^3}(3z^2-1)\hat{e}_z \quad (13b)$$

Equation 13b shows two aspects of the virtual dipole 46. First, virtual dipole 46 generates a magnetic field at point 42 that has a parallel component $$-\frac{m}{|\vec{x}|^3}3z$$

which has the same magnitude of the parallel component of the field from the original dipole but in the opposite direction. Secondly Equation 13b shows that that magnetic field present at the point 42 can be considered a sum of the magnetic fields present due to the real dipole 40 and virtual dipole 46, $\vec{H}_a$ and $\vec{H}'_a$, respectively:

$$\vec{H}_A + \vec{H}'_A = \begin{bmatrix} \frac{m}{|\vec{x}|^3}3zr\hat{e}_r + \\ \frac{m}{|\vec{x}|^3}(3z^2-1)\hat{e}_z \end{bmatrix} + \begin{bmatrix} -\frac{m}{|\vec{x}|^3}3zr\hat{e}_r + \\ \frac{m}{|\vec{x}|^3}(3z^2-1)\hat{e}_z \end{bmatrix}$$

(From Equations 9b and 13b above)

$$= 2\frac{m}{|\vec{x}|^3}(3z^2-1)\hat{e}_z \quad (14)$$

This means that the field produced by virtual dipole 46 cancels the parallel component of the field produced by the real dipole 40. This also means that, due to the effect of the shield, the normal component of the magnetic field at the interface is twice the magnitude it would be if the shield was not present.

Figure 3:
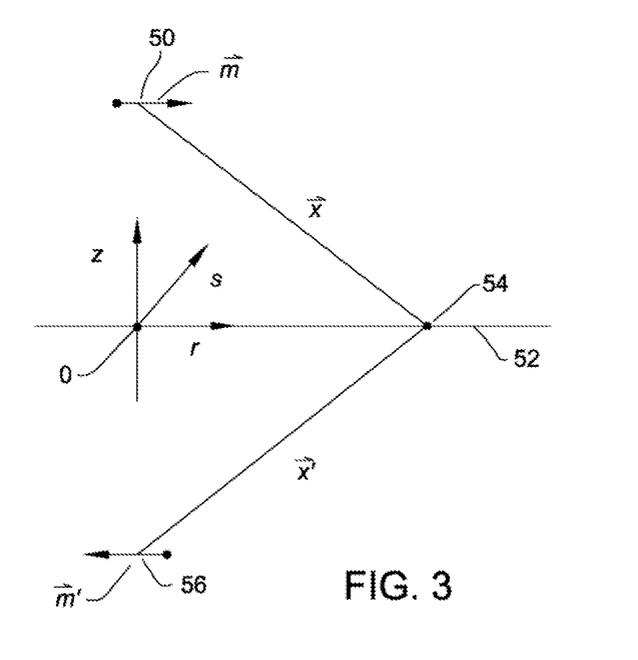
FIG. 3 is a diagrammatic representation of device that emits electromagnetic energy, a real dipole, parallel to the shield-air interface and the virtual dipole formed by the shield.

FIG. 3 illustrates the effect of the presence of the shield when there is a real dipole 50 parallel to the shield-air boundary. Equation 6 above remains a valid equation for determining the strength of the magnetic field $\vec{H}_A$ present on the air side of point 54 of line 52 if the line is just an axis, not a shield-air boundary. The location of real dipole 50 is defined in an r-s-z Cartesian coordinate system wherein the z-axis is perpendicular to line 52. In this coordinate system: $\hat{e}_z$ is the unit vector along the z axis; $\hat{e}_r$ is the unit vector for the r axis; and $\hat{e}_s$ is the unit vector s axis, the cross product of $\hat{e}_z$ and $\hat{e}_r$. The axes intersect at origin point O. The magnitude of the dipole, $\vec{m}$, and the unit vector $\hat{x}$ of vector $\hat{x}$ from the dipole to point 54 are defined as:

$$\vec{m}=m_r\hat{e}_r+m_s\hat{e}_s \quad (15)$$

and $$\hat{x}=r\hat{e}_r+z\hat{e}_z \quad (16; \text{Same as Equation 11})$$

Accordingly, by the substitution of Equations 15 and 16 into Equation 6, the components of the magnetic field real dipole 50 places on point 54 when the shield is not present decomposes as follows:

$$\vec{H}_A = \frac{3\hat{x}(\hat{x}\cdot\hat{m})-\hat{m}}{|\vec{x}|^3} \quad \text{(Equation 6)}$$

$$= \frac{1}{|\vec{x}|^3}(3(r\hat{e}_r+z\hat{e}_z)rm_r-(m_r\hat{e}_r+m_s\hat{e}_s)) \quad (16a)$$

$$= \frac{1}{|\vec{x}|^3}m_r(3r^2-1)\hat{e}_r - \frac{1}{|\vec{x}|^3}m_s\hat{e}_s + \frac{1}{|\vec{x}|^3}3m_rzr\hat{e}_z \quad (16b)$$

The above means that the normal component of the magnetic field at point 54 is $$\frac{1}{|\vec{x}|^3}3m_rzr;$$

the parallel component is $$\frac{1}{|\vec{x}|^3}m_r(3r^2-1)\hat{e}_r - \frac{1}{|\vec{x}|^3}m_s\hat{e}_s.$$

If a shield is present at line 52, (assume the shield extends into and outside of the paper,) the magnetic field present at point 54 changes. Specifically as discussed above, the parallel component of the magnetic field, $$\frac{1}{|\vec{x}|^3}m_r(3r^2-1)\hat{e}_r - \frac{1}{|\vec{x}|^3}m_s\hat{e}_s,$$

is canceled by another magnetic field.

The system and method of this invention again assumes that the parallel component of the magnetic field produced by real dipole 50 is cancelled by a complementary field emitted by a virtual dipole 56. Virtual dipole 56 is located at a position that is a mirror across line (shield) 52 at which real dipole 50 is located. Accordingly, vector $\vec{x}'$ and vector $\hat{x}'$ are, respectively, the vector and unit vector from virtual dipole 56 to point 54. Vector $\vec{m}'$ is the magnitude and direction of the virtual dipole 56. Therefore, $$\vec{m}' = -\vec{m} = -m_r \hat{e}_r - m_s \hat{e}_s \qquad (17)$$

$$\hat{x}' = r\hat{e}_r - z\hat{e}_z \qquad (18)$$

and $$|\vec{x}'| = |\vec{x}| \qquad (19; \text{Same as Equation 12})$$

Thus, the magnetic field that can be considered present at point 54 due to the virtual dipole 56 is:

$$\vec{H}'_a = \frac{3\hat{x}'(\hat{x}' \cdot \vec{m}') - \vec{m}'}{|\vec{x}'|^3} \qquad \text{(From Equation 6)}$$

$$= \frac{1}{|\vec{x}|^3}(3(r\hat{e}_r - z\hat{e}_z)(-rm_r) + (m_r\hat{e}_r + m_s\hat{e}_s)) \qquad (19a)$$

$$= -\frac{1}{|\vec{x}|^3}m_r(3r^2 - 1)\hat{e}_r + \frac{1}{|\vec{x}|^3}m_s\hat{e}_s + \frac{1}{|\vec{x}|^3}3m_r zr\hat{e}_z \qquad (19b)$$

Equation 19b means that that virtual dipole 56 generates a magnetic field at point 54 that a parallel component of $$-\frac{1}{|\vec{x}|^3}m_r(3r^2 - 1)\hat{e}_r + \frac{1}{|\vec{x}|^3}m_s\hat{e}_s$$

which has the same magnitude of the parallel component of the field generated by the real dipole 50 though in the opposite direction.

Accordingly, if magnetic fields generated by the real dipole 50 and virtual dipole 56 at point 54 are added together, the result is:

$$\vec{H}_a + \vec{H}'_a = \qquad \text{(From Equations 16b and 19b)}$$

$$\left[\frac{1}{|\vec{x}|^3}m_r(3r^2 - 1)\hat{e}_r - \frac{1}{|\vec{x}|^3}m_s\hat{e}_s + \frac{1}{|\vec{x}|^3}3m_r zr\hat{e}_z\right] +$$

$$\left[-\frac{1}{|\vec{x}|^3}m_r(3r^2 - 1)\hat{e}_r + \frac{1}{|\vec{x}|^3}m_s\hat{e}_s + \frac{1}{|\vec{x}|^3}3m_r zr\hat{e}_z\right]$$

$$= 2\frac{1}{|\vec{x}|^3}3m_r zr\hat{e}_r \qquad (20)$$

This means that the parallel field of virtual dipole 56 cancels the complementary field of real dipole 50. Again, this also means that the presence of the shield doubles the strength of the magnetic field normal to the shield caused by the real dipole. Thus, the condition that at the shield-air boundary, the only magnetic field is perpendicular to the boundary is satisfied. Since a magnetic field is a continuous field, when a solution satisfies the boundary condition for all boundary points, it will be the solution for the entire volume. Therefore, the virtual dipole can replace the magnetic field change caused by the highly magnetically permeable shield at any point in the volume. Thus, for a real dipole parallel to the shield on one side of the shield, the field change caused by the shield can be replaced by a virtual dipole on the opposed side of the shield. This virtual dipole is located at the mirror image spot of the real dipole relative to the shield, has the same magnitude of the real dipole is directed along a vector parallel and 180° opposite in direction to the real dipole.

Figure 4:
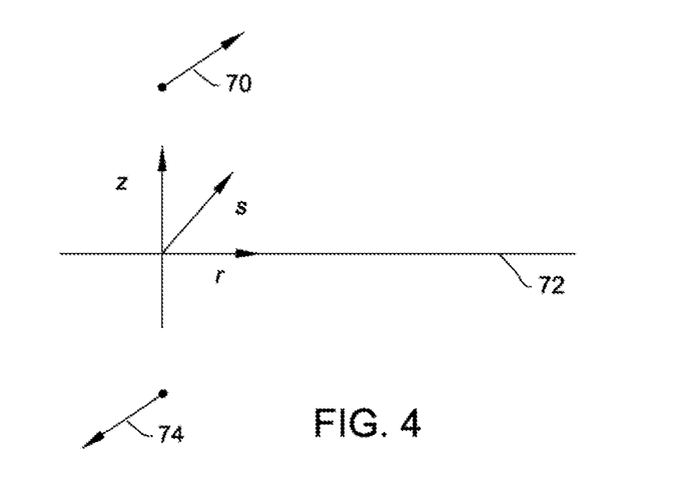
FIG. 4 is a diagrammatic representation of device that emits electromagnetic energy, a real dipole, along a line neither normal nor parallel to the shield-air interface and the virtual dipole formed by the shield.

Any dipole on one side of the shield can be decomposed into a vector having a moment parallel to the shield and a vector having a moment perpendicular to the shield. Therefore, per the above discussion, such a real dipole, for example, dipole 70 of FIG. 4, on one side of a shield 72 can be replaced by a virtual dipole 74 at the mirror image location on the opposed side of the shield. Relative to the real dipole 70, the unit vector of the virtual dipole 74 has its component normal to the shield 72 in the same direction of the real dipole 70. Relative to the real dipole 70, the unit vector of the virtual dipole 74 has its component parallel to the shield 72 at a shift of 180°.

II. Basics of Electromagnetic Navigation

Figure 5:
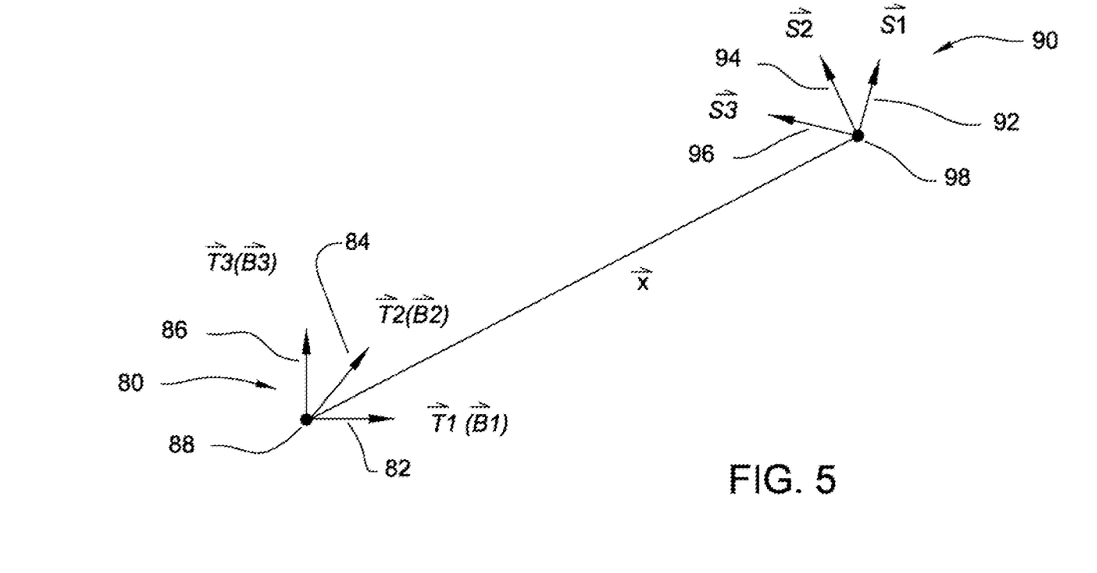
FIG. 5 is a diagrammatic illustration of how the transmitting elements of a navigation system transmitter assembly function as real electromagnetic energy emitting dipoles and the sensor assembly, also of the navigation system, that measures the emitted energy.

The effect the symmetrical property of the shield-formed virtual dipole has on the navigation system is appreciated by understanding the basics of electromagnetic navigation. As depicted in FIG. 5, a surgical navigation system can be considered to comprise a transmitter assembly 80 and a sensor assembly 90. Transmitter assembly 80 includes three transmitters, 82, 84 and 86 in the Figures. The transmitters 82, 84, and 86 are typically in the form of coils. The transmitters 82, 84, 86 are, ideally, mutually orthogonal relative to each other. In preferred systems, including systems of this invention, transmitters 82, 84 and 86 are centered on a common point, point 88 in the Figures. Mathematically, transmitters 82, 84 and 86 are represented by vectors $\vec{T}1$, $\vec{T}2$ and $\vec{T}3$, respectively. For mathematic derivation of this invention, we define a transmitter coordinate system that has its origin at point 88 and its x-, y- and z-axis align along the vectors $\vec{T}1$, $\vec{T}2$ and $\vec{T}3$ of the transmitters 82, 84 and 86, respectively.

Sensor assembly 90 includes three sensors 92, 94, and 96 capable of monitoring the magnetic fields generated by the transmitter assembly 80. The individual sensors may be coils, fluxgate transducers, magnetoresistive sensors, Hall effect sensors or any other devices capable of providing precision measurements of magnetic fields. The individual sensors 92, 94 and 96 are, ideally, mutually orthogonal from each other. Ideally, especially in the system 110 of this invention (FIG. 6), the sensors are also centered on a common point, point 98 in the drawings. Mathematically, sensors 92-96 are considered to be in a set position in a sensor coordinate system with an origin of point 98.

Mathematically, sensors 82, 84 and 86 are represented by vectors $\vec{S}1$, $\vec{S}2$ and $\vec{S}3$, respectively. For mathematic derivation of this invention, we define a sensor coordinate system that has its origin at point 98 and its x'-, y'- and z'-axis align along the vectors $\vec{S}1$, $\vec{S}2$ and $\vec{S}3$ of the sensors 82, 84 and 86, respectively.

Figure 6:
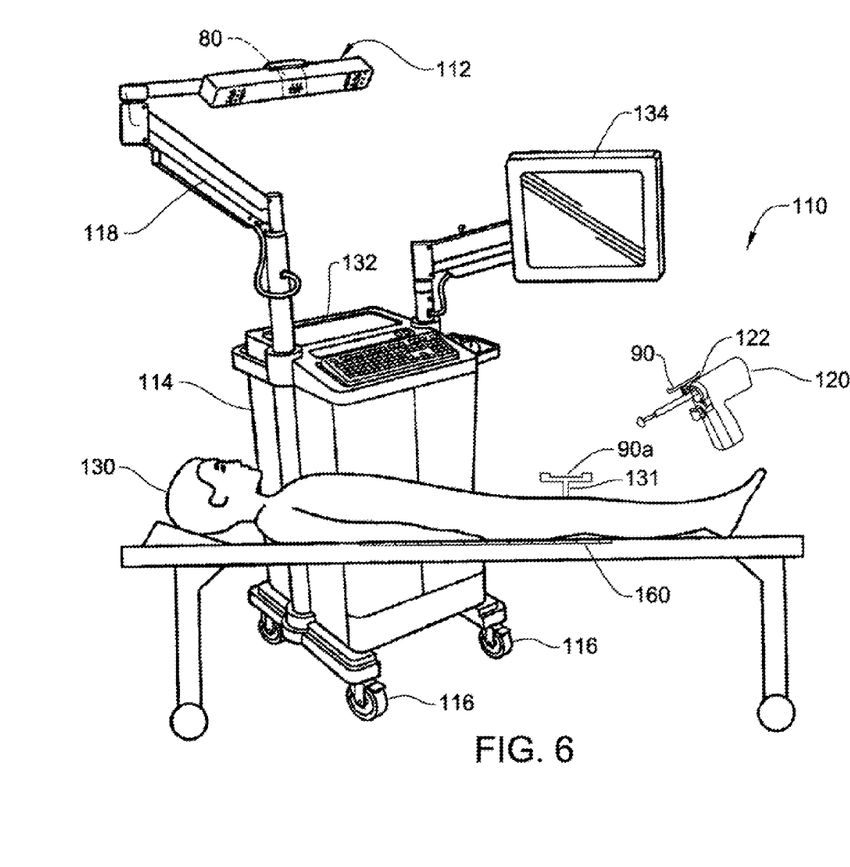
FIG. 6 is a view of the basic components of a surgical navigation system of this invention.

As seen in FIG. 6, navigation system 110 of this invention is constructed so that the transmitter assembly 80 is, relative to sensor assembly 90, at a fixed location. More particularly, transmitter assembly 80 (shown as a rectangular box) is contained in a localizer 112. The localizer 112 is attached to a base unit 114. Base unit 114 is mounted on casters 116 to provide the unit with mobility. A flexible linkage 118 suspends the localizer 112 above the base unit. Linkage 118 allows the localizer 112 to be selectively positioned relative to base unit 114.

Sensor assembly 90 is attached to the object the position and orientation of which is to be tracked. In FIG. 6, this object is a medical handpiece 120. The unit containing sensors assembly 90, sensors 92-96, is often referred to as the tracker 122. Tracker 122 is typically the physical unit of system 110 attached to the object the position and orientation of which is to be tracked. The sensor coordinate system is fixed relative to the tracker 122. In the basic construction of system 110 of this invention, there is a single localizer 112 and several trackers 122 (one shown). Each tracker 122 tracks an individual object so that system 110 tracks multiple objects. In the depicted system 110 of FIG. 6, the system is employed to determine the position of a surgical tool, instrument or implant relative to a surgical site on a patient 130.

While not shown, it should also be understood that often one or more trackers may be physically attached to the patient adjacent the surgical site. Sometimes these trackers are called "markers". System 110 using the below described process, determines the position and orientation of these markers relative to the localizer 112.

The measurements of magnetic field strength made by sensors 92-96 are applied to a processor 132 integral with the base unit 114. Often, this signal transfer is by a wireless RF connection. Other wireless signal transfer mechanisms such as infra-red connections may be used to establish some or all of these connections. Wired connections may also be employed. The particular means by which the sensor signals are transmitted to system processor 132 are not relevant to this invention. Hence, no specific signal exchange assembly is shown.

In some alternative systems of this invention, the transmitter assembly 80 is attached to the object to be tracked and the sensor assembly 90 is at a fixed location, (mounted to the localizer).

The object of the navigation process is to determine the geometrical relationship between the sensor coordinate system and the transmitter coordinate system. This makes it possible to transform position and orientation data in the sensor coordinate system, the coordinate system of tracker 122, to the transmitter coordinate system, the coordinate system of localizer 112, and vice verse. Using these transformations, all the objects tracked are placed in a common coordinate system even if the objects shift positions and orientations. The relationships between the transmitter coordinate system and the sensor coordinate system are represented by a translation vector $\vec{x}$ and a rotational matrix R. Vector $\vec{x}$ is the vector from point 88, the origin of transmitter coordinate system internal to the localizer 112, to point 98, the origin of sensor coordinate system internal to the tracker 122.

Rotational matrix R represents the rotation that aligns the x'-, y'- and z'-axes of the sensor coordinate system to the x-, y- and z-axes of transmitter coordinate system. If $\hat{e}'_x$, $\hat{e}'_y$, $\hat{e}'_z$ represent the unit vectors of, respectively, the x'-, y'- and z'-axes of the sensor coordinate system, referenced to transmitter coordinate system, rotational matrix R can be written as:

$$R = [\hat{e}'_x, \hat{e}'_y, \hat{e}'_z] = \begin{bmatrix} e'_{xx} & e'_{yx} & e'_{zx} \\ e'_{xy} & e'_{yy} & e'_{zy} \\ e'_{xz} & e'_{yz} & e'_{zz} \end{bmatrix} \quad (21)$$

Each matrix element $e'_{ij}$ is the product of a matrix multiplication process wherein the multipliers are sin and cos matrix elements of three (3) individual 3×3 matrixes that, respectively, define the yaw, pitch and roll of the axes of the sensor coordinate system around the axes of the transmitter coordinate system. Here, "yaw" is understood to be rotation about the z axis of the transmitter coordinate system; "pitch" is rotation about the y axis of the transmitter coordinate system; and "roll" is rotation about the x axis of the transmitter coordinate system.

Transmitters 82, 84 and 86 generate separate magnetic fields. The magnetic fields emitted by transmitters 82, 84 and 86 are mathematically represented as vectors $\vec{B}1$, $\vec{B}2$ and $\vec{B}3$, respectively. Each transmitter 82, 84 and 86 can be considered to be a distinct magnetic dipole. Accordingly, the particular magnetic field $\vec{B}i$ emitted by transmitter $\vec{T}i$ present at location $\vec{x}$ is defined by Equation 6 above. Thus, the magnetic fields collectively present at point 98 are described by magnetic field matrix Bm, where:

$$Bm = [\vec{B}1 \vec{B}2 \vec{B}3] \quad (22)$$

Each sensor 82, 84 and 86, measures the strength of each of the three magnetic fields. Thus, at a given location and orientation, the following measurements are obtained:

$$M = \begin{bmatrix} m_{11} & m_{12} & m_{31} \\ m_{21} & m_{22} & m_{23} \\ m_{31} & m_{32} & m_{33} \end{bmatrix} \quad (23)$$

where $m_{ij}$ is the strength of the magnetic field based on the field emitted from transmitter i measured at sensor j. The above matrix is the measurement matrix M. Each measured value $m_{ij}$ of magnetic field strength is based on the magnetic field $\vec{B}i$ being measured by sensor $\vec{S}j$ according to the following formula:

$$m_{ij} = \vec{B}i \cdot \vec{S}j \quad (24)$$

Each sensor vector $\vec{S}j$ aligns with the associated axis j, unit vector $\hat{e}_j$, in the sensor coordinate system. Therefore, the following equation also holds true:

$$m_{ij} = \vec{B}i \cdot \hat{e}_j \quad (25)$$

It should be understood that in each of Equations it is assumed the measurements of the magnetic field strength are normalized for both variations in the strengths of the signals output by the transmitters 82, 84 and 86 an variations in the sensitivities of the sensors 92, 94 and 96.

Thus, the nine measured magnetic field values are used to solve for six unknowns, the three variables representative of position vector $\vec{x}$ and the three variables representative of the orientation of the sensor coordinate system and, therefore, the object to be tracked, relative to the transmitter coordinate system.

Algorithms such as those provided in U.S. Pat. No. 4,287, 809, Helmut-Mounted Sighting System, issued 8 Sep. 1981, U.S. Pat. No. 4,314,251, Remote Object Position And Orientation Locater, issued 2 Feb. 1982 and U.S. Pat. No. 4,945,305, Device For Quantitatively Measuring The Relative Position And Orientation Of Two Bodies In The Presence Of Metals Utilizing Direct Current Magnetic Fields, issued 31 Jul. 1990 are employed to, based on the magnetic field measurements, determine the position and orientation of the sensor assembly 90. Each of the above-cited documents is incorporated herein by reference. Another document that provides an overview of the surgical navigation process is the Applicant's U.S. patent application Ser. No. 11/123,985, System And Method For Electromagnetic Navigation In The Vicinity OF A Metal Object, U.S. Patent Pub. No. US 2006/0264732 A1, also incorporated herein by reference.

Processor 132, based on the measurements of magnetic field strength made by sensor assembly 90, generates data indicating the position and orientation of tracker 122 relative to the localizer 112. By induction, this leads to the knowledge of the position and orientation of the associated medical instrument 120. Often, especially with a surgical navigation system 110, this information is presented on a display 134 also part of the base unit 114.

While the above incorporated-by-reference documents provide an understanding of how sensor assembly position and orientation is determined, a further understanding of the navigation process is useful for understanding the system and method of this invention. Substituting Equation 6 into Equation 25 yields the following relationship between the magnetic field measured by a sensor j based on the energy emitted by a transmitter I for each component of the measurement matrix M:

$$m_{ij} = \frac{3(\hat{x} \cdot \hat{e}_i)\hat{x} - \hat{e}_i}{|\vec{x}|^3} \cdot e_j \tag{26a}$$

$$= \frac{3(\hat{x} \cdot \hat{e}_i)(\hat{x} \cdot e_j) - (\hat{e}_i \cdot e_j)}{|\vec{x}|^3} \tag{26b}$$

Here, i=1, 2, 3 and j=1, 2, 3. Matrix elements $m_{ij}$ are symmetrical with regard to $\hat{e}_i$ and $e_j$. This symmetry is apparent in from Equation 26b and its associative alternative, Equation 26c:

$$m_{ij} = \frac{3(\hat{x} \cdot \hat{e}_i)(\hat{x} \cdot e_j) - (\hat{e}_i \cdot e_j)}{|\vec{x}|^3} \tag{26b}$$

$$= \frac{3(\hat{x} \cdot e_j)(\hat{x} \cdot \hat{e}_i) - (e_j \cdot \hat{e}_i)}{|\vec{x}|^3} = m'_{ji} \tag{26c}$$

Here, symbol m' is used to represent the measurement matrix of this associative change from Equation 26b to Equation 26c. Physically, this means if the transmitter assembly 80 and the sensor assembly 90 exchange roles in forming the measurement matrix elements will have the same values. However, owing to this transformation, j is the transmitter index and i is the sensor index. Comparing the matrix elements $m_{ij}$ and $m'_{ji}$ side by side, the following relationship is apparent:

$$M' = \begin{bmatrix} m'_{11} & m'_{12} & m'_{13} \\ m'_{21} & m'_{22} & m'_{23} \\ m'_{31} & m'_{32} & m'_{33} \end{bmatrix} = \begin{bmatrix} m_{11} & m_{21} & m_{31} \\ m_{12} & m_{22} & m_{32} \\ m_{13} & m_{23} & m_{33} \end{bmatrix} = M^T \tag{27}$$

In other words, from the substitutions of Equation 26b and 26c it can be seen in Equation 27 that when these substitution is performed, the role changed measurement matrix M' is the transpose of the original measurement matrix M of Equation 23.

III. Implementation

Figure 7:
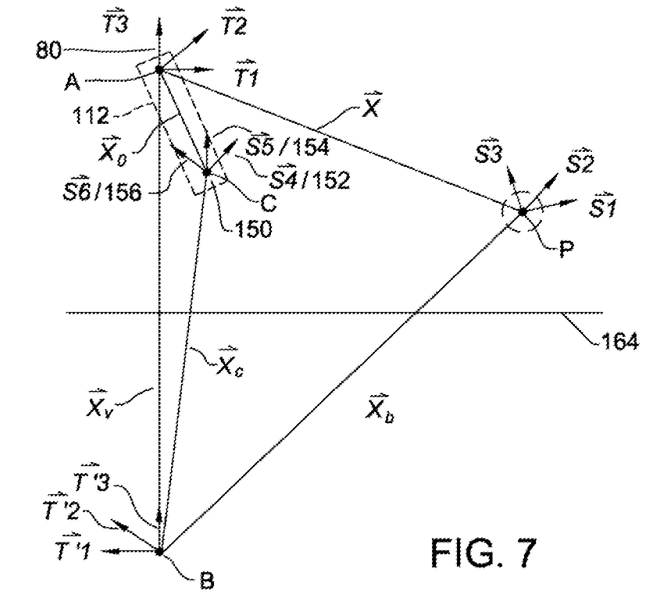
FIG. 7 is a diagrammatic illustration of the transmitter and sensor assembly internal to the localizer, the sensor assembly internal to the tracker and the virtual dipole and the relative positions of these elements of the invention.

As seen in the block illustration of FIG. 7, localizer 112 and tracker 122, the localizer of the system 110 of this invention includes its own sensor assembly, correction sensor assembly 150. (To distinguish the two sensor assemblies 90 and 150, sensor assembly 90 is now referred to as "tracker sensor assembly 90.") Correction sensor assembly 150 includes three mutually orthogonal sensor elements 152, 154 and 156. Sensor elements 152, 154 and 156 are understood to be aligned with vectors $\vec{S}4$, $\vec{S}5$ and $\vec{S}6$, respectively. The correction sensor assembly 150 is, like transmitter assembly 80, firmly attached to the localizer 112. This means that elements of the offset vector $\vec{x}_O$ from the center point A of transmitter assembly 80 to center point C of the correction sensor assembly 150 are known. Thus, at manufacture, in an environment free of electromagnetic interference a reference matrix $M^O$ of measurements made by correction sensor elements 152, 154, and 156 of the electromagnetic energy emitted by transmitter elements 82, 84 and 86 is generated:

$$M^O = \begin{bmatrix} m^O_{11} & m^O_{12} & m^O_{13} \\ m^O_{21} & m^O_{22} & m^O_{23} \\ m^O_{31} & m^O_{32} & m^O_{33} \end{bmatrix} \tag{28}$$

Matrix $M^O$, for reasons apparent below, is referred to as the calibrated measurement matrix.

In system 110 of this invention, a shield 160 (FIG. 6) formed of highly magnetically permeable material ($\mu_{SHIELD}/\mu_{AIR} > 10^4$,) is disposed underneath the patient 130. In some implementations of the invention, the shield is not sized to fit under the whole of the operating table on which the patient is disposed. Rather the shield is of a size less than the operating table and is positioned underneath the portion of the body of the patient at which the surgical instruments, including implants, to be tracked are placed. In FIG. 7 it should be understood that shield is represented by a line 164 that represents the plane of the shield that extends both into and out of the paper.

As discussed above, owing to the presence of shield 160, in this invention, virtual dipoles are considered to be present opposite the real dipoles that are present when transmitter elements 82, 84 and 86 are actuated. In FIG. 7, vector $\vec{T}1'$ is the virtual dipole that corresponds to the real dipole $\vec{T}1'$ produced by transmitter element 82. Vector $\vec{T}2'$ is the virtual dipole that corresponds to the real dipole $\vec{T}2$ produced by transmitter element 84. Vector $\vec{T}3'$ is the virtual dipole that corresponds to the real dipole $\vec{T}3$ produced by transmitter element 86. Virtual dipoles $\vec{T}1'$, $\vec{T}2'$ and $\vec{T}3'$ originate at point B. Point B is on a line normal to the shield 160 that extends through point A, the center of the transmitter assembly 80. In FIG. 7, localizer 112 is seen as a phantom rectangle; tracker 122 is a phantom circle.

Thus, when system 110 is used to determine the location of tracker 122, six vectors of interest are present: vector $\vec{x}$, the vector from the origin of the localizer transmitter assembly 80 (the original of the real dipoles,) point A, to the origin of the tracker sensor assembly 90, point P; the above-described offset vector $\vec{x}_O$; vector $\vec{x}_C$, the vector from origin of the virtual dipoles, point B, to the origin of the correction sensor assembly 150; vector $\vec{x}_V$, the vector from the origin of the real dipoles to the origin of the virtual dipoles; and vector; and vector $\vec{x}_b$, the vector from the origin of the virtual dipoles to the origin of the tracker sensor assembly 90.

Vectors $\vec{x}_C$, $\vec{x}_O$ and $\vec{x}_V$ have the following relationship:

$$\vec{x}_v = R_O \vec{x}_C + \vec{x}_O \tag{29}$$

Here, $R_O$ is the rotational matrix that rotates the x, y and z axes of the transmitter coordinate system to, respectively, the $x_c$, $y_c$ and $z_c$ of the correction sensor assembly coordinate system. Rotation matrix $R^V$ defines the rotation of the virtual dipoles around point B relative to the orientation of the real dipoles around point A Rotation matrix $R^V$ is defined by the following relationship:

$$R^V = R_O R_C^V \tag{30}$$

Rotation matrix $R_C^V$ is the rotation of virtual dipoles relative to the sensors of correction sensor assembly 150.

Figure 8A:
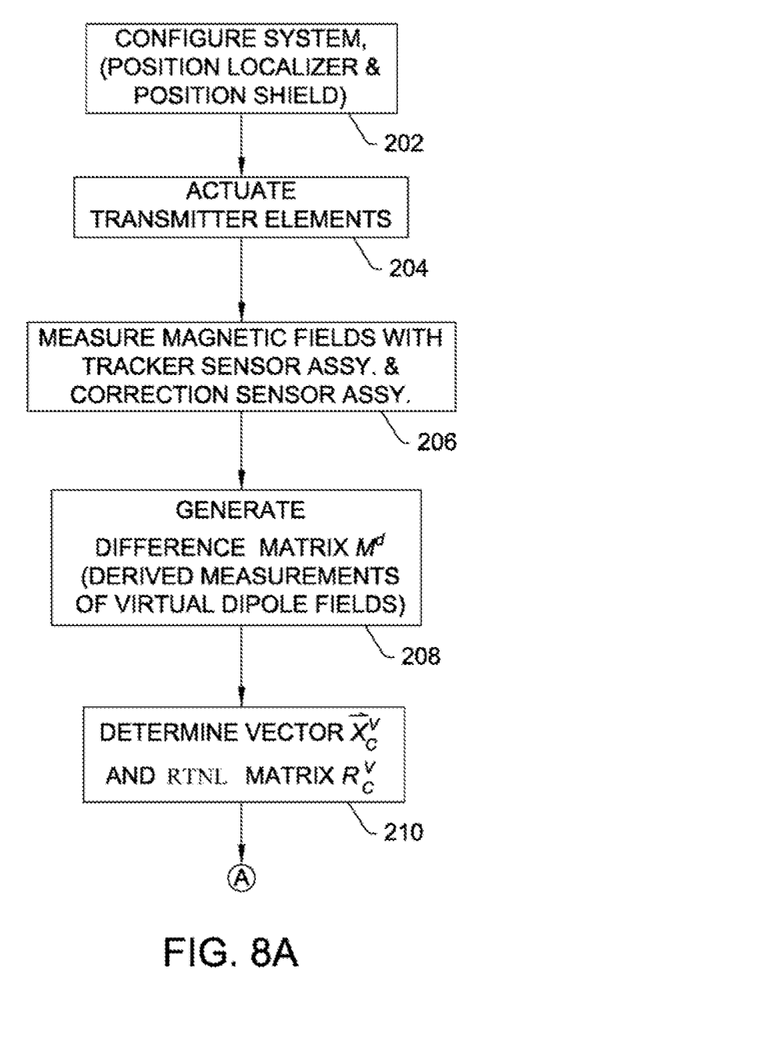
FIGS. 8A and 8B collectively form a flow chart of the process steps executed by the system and method of this invention to find the location of the moving tracker relative to the static localizer.
Figure 8B:
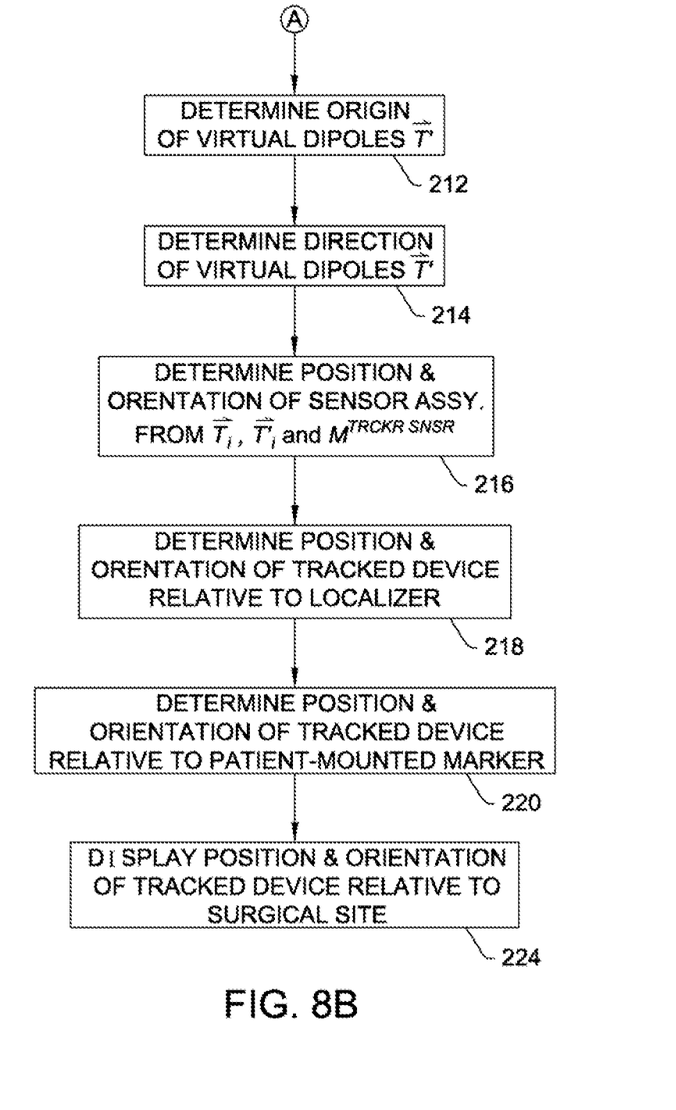

FIGS. 8A and 8B illustrate how the above fundamental relationships are used in the surgical navigation process to determine the position and orientation of the tracker 122. Initially, in a step 202, system 110 of this invention is configured for use. As part of step 202, the shield 160 is placed beneath the patient 130 at the location at which the surgical procedure is to be performed. Also in step 160, the localizer 112 and base unit 114 are positioned so that the localizer can be placed in a location near the patient where it can track the objects that need to be tracked. An addition sub-step of step 202 is the fitting of trackers 122 to the medical instruments and/or implants the position(s) of which is(are) to be tracker.

Step 204 is the actual start of the navigation process. In step 204, transmitter elements 82, 84 and 86 are actuated. The above-cited, incorporated-by-reference application Ser. No. 11/123,985 describes several means by which the transmitter elements are simultaneously actuated. As a result of the actuation of the transmitter elements 82, 84 and 86, inherent in step 204, three separate magnetic fields, $\vec{B}1$ $\vec{B}2$ and $\vec{B}3$ are emitted by the transmitter assembly 80.

Consequently, in a step 206, the three magnetic fields are measured by both the tracker sensor assembly 90 and the correction sensor assembly 150. Also as part of step 206, these sensor signals are normalized and forwarded to the base unit processor 132. In some versions of the invention, the normalization of the sensed measurements of magnetic field strength, at least for variation in individual sensor elements of the particular sensor assembly 90 or 150, is performed by a processor integral with the sensor assembly. Alternatively, after the two sets of three (3) sensor element signals each are received by the base unit processor 132, processor 132 performs the following functions: normalizes each sensor signal in the set of signals to account for variations in sensor sensitivity; deconstructs each sensor signal into its three separate components (one from each of the transmitted electromagnetic waves); and normalizes each deconstructed sensor signal component to account for variations in transmission strength.

As a consequence of the signal processing of step 206, an ambient measurement matrix $M^C$ of the measurements of the magnetic fields measured by correction sensor assembly elements 152, 154 and 156. Thus, matrix elements $m_{ij}^c$ correspond to matrix elements $m_{ij}^O$ of the matrix $M^O$ of Equation 28 except that they are magnetic strength measurements made during the performance of the surgical procedure. If the shield was not present, the elements of the ambient measurement matrix should be equal to those of the calibration measurement matrix, $M^C = M^O$.

However, in the system of this invention, shield 160 is present. The shield interferes with the transmission of the electromagnetic waves from the transmitter assembly 80 to the correction sensor assembly 150, thus $M^C \neq M^O$.

However as discussed above, the changes in magnetic field caused by shield 160 can be considered to be the changes caused by the presence of virtual dipoles $\vec{T}'1$, $\vec{T}'2$, and $\vec{T}'3$. Accordingly, in a step 208 a difference matrix $M^j$ is determined according to the following equation:

$$M^d = M^C - M^O = \begin{bmatrix} m_{11}^d & m_{12}^d & m_{13}^d \\ m_{21}^d & m_{22}^d & m_{23}^d \\ m_{31}^d & m_{32}^d & m_{33}^d \end{bmatrix} \tag{31}$$

These derived values of the elements of difference matrix $M^d$ are based on the signal changes caused by the virtual dipoles. In other words, the measurements of matrix elements $m_{ij}^d$ are the derived measurements of the electromagnetic fields emitted by virtual dipoles $\vec{T}'1$, $\vec{T}'2$, and $\vec{T}'3$ as measured by correction sensors 152, 154 and 156.

Based on these derived measurements of magnetic field strength, in a step 210, the location of the origin of the virtual dipoles, point B relative to the origin of the correction sensor assembly, vector $\vec{x}_c$ is calculated. Also in step 210 the rotational matrix $R_c^v$ of the virtual dipoles $\vec{T}'1$, $\vec{T}'2$, and $\vec{T}'3$ around axes $\vec{S}4$, $\vec{S}5$ and $\vec{S}6$ of the correction sensor elements 152, 154 and 156, respectively, is calculated. Specifically, vector $\vec{x}_c$ and rotation matrix $R_c^v$ can be calculated based on the fact that transpose of difference matrix $M^d$ and the conventional magnetic localizer algorithms can be used to calculate the position of point B from point C and the rotation of the virtual dipoles relative to the correction sensor elements. Then, in a step 212, using Equations 29 and 30 above, the position and orientation of the virtual coordinate system relative to the origin of transmitter assembly 80, respectively, vector $\vec{x}_v$ and rotation matrix $R^V$ are obtained.

Then, in a step 214, the direction of the virtual dipoles, the virtual transmitters, is determined by processor 132 according to the following relationships.

$$\vec{T}'1 = \hat{e}_x^v = R^v \cdot \begin{bmatrix} 1 \\ 0 \\ 0 \end{bmatrix} \tag{32}$$

$$\vec{T}'2 = \hat{e}_y^v = R^v \cdot \begin{bmatrix} 0 \\ 1 \\ 0 \end{bmatrix} \tag{33}$$

$$\vec{T}'3 = \hat{e}_z^v = R^v \cdot \begin{bmatrix} 0 \\ 0 \\ 1 \end{bmatrix} \tag{34}$$

Once step 214 is executed, processor 132 has data that indicates the orientation of both the real dipoles $\vec{T}_i$ and the virtual dipoles $\vec{T}'_i$. Any given sensor element $\vec{S}_j$, therefore measures the following magnetic field:

$$m_{ij} = \vec{B}_{ij} = \left[ \frac{3(\hat{x} \cdot \vec{T}_i)\hat{x} - \vec{T}_i}{|\vec{x}|^3} + \frac{3(\hat{x}_b \cdot \vec{T}'_i)\hat{x} - \vec{T}'_i}{|\vec{x}_b|^3} \right] \cdot \vec{S}_j \quad (35)$$

The first addend of Equation 35 is the contribution of the real dipole to the measured magnetic field. The second addend is the contribution of the virtual dipole.

Thus, in a step 216, Equation 35 is solved to find the values the coordinates from the origin of the real dipole (transmitter assembly 80) that define vector $\vec{x}$ and the yaw, pitch and roll values, the coordinates that define vectors $\vec{S}_j$, that define the orientation of the tracker sensor assembly 90 relative to the transmitter assembly. It should be understood that in Equation 35 the known values are the nine values of the matrix elements $m_{ij}$ and the coordinates of vectors $\vec{T}_i$ and $\vec{T}'_i$.

Typically, an iterative process is used to solve Equation 35. Often the first step in this process involves ignoring the virtual dipole, setting $\vec{T}'_i = 0$. Based on the initial estimate of vector $\vec{x}$ and vectors $\vec{S}_j$ from this assumption, additional estimates of these parameters are generated based on the resultant values of matrix elements $m_{ij}$ calculated based on these estimated parameters. In successive iterations in which the matrix elements are determined, vector $\vec{T}'_i$ is then used as an input variable along with vector $\vec{T}_i$ and the estimates of vector $\vec{x}$ and vectors $\vec{S}_j$ to determine values for the matrix elements $m_{ij}$. One algorithm that can be used in this iterative process is the Levenberg-Marquardt method.

Thus, as result of the execution of step 216, data indicating the position and orientation of the sensor assembly 90 relative to transmitter assembly 80 are generated. By induction, these data, in step 218, lead to indicating the position and orientation of the medical device attached to the tracker 122.

As mentioned above, typically at least one tracker/marker is also attached to the patient adjacent the surgical site. System processor 132 uses the above described method to determine the position and location of this tracker/marker relative to the localizer. Accordingly system processor 132 generates data indicating the position and orientation of both the patient mounted tracker/marker and the instrument tracker 122 relative to the localizer 112. In a step 220 system processor 132 then determines the position and orientation of the tracker relative to the patent-mounted tracker/marker. System processor 132 is therefore, in step 224 able to present on display 134 an image or other data indicating the position and orientation of the tracked medical device relative to the fixed reference point on the patient.

While not illustrated, it should be appreciated that, after the data indicating the position and orientation of the tracked medical device is generated and displayed, the process repeats starting with the reexecution of step 204. In the subsequent executions of step 216, it should be understood that the initial estimated values for vector $\vec{x}$ and vectors $\vec{S}_j$ are the values calculated for these parameters in the last execution of step 216.

It should also be appreciated that similar signals are exchanged between transmitter 80 and a second sensor assembly 90a. Sensor assembly 90a is fitted to the patient. In the illustrated version of the invention, sensor 90a is shown fitted to a post 131 that is firmly attached to and extends above the patient Then, using the above described method, processor 132 determines the position and orientation of sensor assembly 90a relative to transmitter assembly 80. Processor 132 thus contains data that describes the positions and orientations of both sensor 90 and sensor 90a relative to localizer 112. Based on these data, processor determines the position and orientation of the surgical tool 120 relative to the patient, or a surgical site on the patient. These data can then be presented on display 134 as an aid to the surgeon.

System 110 of this invention is provides position and orientation data for a tracked medical device. The system includes a shield 160 that is placed adjacent the location on the body of at which the tracking is to occur. Further the system of this invention is designed to allow the localizer 112 to be positioned so that, relative to the device tracker 122, the localizer is further spaced from the shield 160. Thus the system of this invention provides shielding around the surgical site and does not require the unwieldy and potentially expensive placement of the localizer between the shield and the tracker.

Since the localizer of this invention does not have to be located 112 between the shield 160 and tracker 122, the localizer can be made mobile. This allows medical personnel to place the localizer in relatively close proximity to the patient. This, in turn means that it is only necessary to rely on relatively lower powered EM emissions to produce the fields needed to determine tracker position and orientation. A benefit of this feature of the invention is that it reduces the likelihood that metal objects against which the shield cannot function as interference barrier do not adversely affect the EM waves that are transmitted from the localizer to the tracker. This, in turn, contributes to the accuracy of the position and orientation measurements made by the system of this invention.

Further in this invention, the transmitter assembly 80 and correction sensor assembly 150 can be spaced relatively far distances from the shield. In most versions of this invention it is anticipated that these assemblies, and therefore the localizer 112 in which they are housed, can be spaced at least 0.2 meters from the shield. In many versions of the invention, the transmitter assembly and correction sensor assembly 150 are spaced 0.5 meters or more from the shield. In other versions of the invention, the transmitter assembly 80 and correction sensor assembly 150 can be positioned 1.0 meters or more from the shield. This means that the localizer 112 and base unit of this invention can be placed a relatively large distance away from the surgical site so the presence of these devices in the operating room do not pose an obstacle adjacent the site.

It should be appreciated that the foregoing is directed to one specific version of the system of this invention. For example, there is no requirement that in all versions of the invention, the relatively static localizer carry both the transmitter assembly and the correction sensor assembly and the tracker sensor assembly be fitted to the tracker. In alternative versions of this invention, the transmitter assembly and correction sensor assembly may be in the tracker and the tracking sensor assembly may be in the localizer.

Also, while it is preferred that the transmitter assembly 80 emit EM waves along the three axes and the tracker and correction sensor assemblies measure EM waves in the three axes, this is not required. In some versions of the invention the transmitter assembly may comprise less than three transmitter elements and/or the relative orientations of the elements may be different from what has been described. Similarly, in other versions of the invention, the tracker sensor assembly and/or the correction sensor assembly may have less than three sensor elements and/or the orientation of the elements may be different from what has been described.

The location of the sensor 90*a* is not limited to what is shown in FIG. 6. For example, sensor 90*a* can also be fixated to the bone of patient beneath the skin.

Therefore, it is an object of the appended claims to cover all such variations and modifications that come within the true spirit and scope of this invention.

What is claimed is:

1. A surgical navigation system comprising:
   a transmitter assembly with at least one transmitter element capable of emitting electromagnetic energy, each said transmitter element, when emitting electromagnetic energy, being considered a real dipole;
   a correction sensor assembly with at least one sensor element capable of sensing electromagnetic energy wherein, relative to said transmitter assembly, said correction sensor assembly is at a fixed position and orientation so as to form a transmitter-correction sensor assembly;
   a tracker sensor assembly with at least one sensor element capable of sensing electromagnetic energy, wherein one of said transmitter-correction sensor assembly or said tracker sensor assembly is moveable relative to the other of said tracker sensor assembly or said transmitter-correction sensor assembly and one of said transmitter-correction sensor assembly or said tracker sensor assembly is part of a tracker attached to a surgical tool;
   a shield formed of magnetically permeable material that is positioned so that a patient, said transmitter-correction sensor assembly and said tracker sensor assembly are located on one side of said shield and are both moveable relative to said shield; and
   a processor connected to said tracker sensor assembly to receive at least one measurement of electromagnetic field strength from said tracker sensor assembly at least one sensor element and to said correction sensor assembly to receive at least one measurement of electromagnetic field strength from said correction sensor at least one sensor element and said processor being configured to:
     based on the at least one measurement of electromagnetic field strength from said correction sensor assembly at least one sensor element, determine the location of at least one virtual dipole, the at least one virtual dipole being located on the side of shield opposite the side on which said transmitter-correction sensor assembly is located;
     based on the location of the at least one real dipole, the location of the at least one virtual dipole and the at least one measurement of electromagnetic field strength of the at least one tracker sensor assembly at least one sensor element, determine the position and orientation of said tracker sensor assembly relative to said transmitter assembly.

2. The surgical navigation system of claim 1, wherein, relative to said tracker sensor assembly, said transmitter-correction sensor assembly is positioned further from said shield.

3. The surgical navigation system of claim 1, wherein said transmitter-correction sensor assembly is attached to a base unit and, relative to said shield, said base unit is mobile.

4. The surgical navigation system of claim 1, wherein said transmitter-correction sensor assembly is moveable relative to said shield and is positioned at least 0.2 meters from said shield.

5. The surgical navigation system of claim 1, wherein said transmitter assembly includes a plurality of transmitters.

6. The surgical navigation system of claim 1, wherein said tracker sensor assembly includes a plurality of sensor elements.

7. The surgical navigation system of claim 1, wherein said correction sensor assembly includes a plurality of sensor elements.

8. The surgical navigation system of claim 1, wherein said processor determines the location of the virtual dipole based on the at least one difference between an at least one measurement made by said correction sensor assembly of electromagnetic energy emitted by said transmitter assembly when said shield is present and an at least one measurement by said correction sensor assembly of electromagnetic energy emitted by said transmitter assembly when said shield is not present.

9. The surgical navigation system of claim 1, wherein:
   a second one of said tracker sensor assembly or a second said transmitter-correction sensor assembly is adapted for attachment to the patient; and
   said processor is able to determine the position of said second tracker sensor assembly relative to said transmitter assembly or of said second transmitter-correction sensor assembly relative said tracker sensor assembly and from that position data and the position of said tracker sensor assembly relative to said transmitter assembly, the position of the surgical tool relative to the patient.

10. The surgical navigation system of claim 1, wherein:
    said shield is positioned to be adjacent the patient:
    said tracker sensor assembly is attached to the surgical tool and is located further from said shield than the distance the patient is located from said shield; and
    said transmitter-correction sensor assembly is located further from said shield than the distance said tracker sensor assembly is located from said field and said transmitter-correction sensor assembly is located at least 0.5 meters from said shield.

11. The surgical navigation system of claim 1, wherein:
    relative to said tracker sensor assembly, said transmitter-correction sensor assembly is spaced further from said shield; and
    said tracker-correction sensor assembly is spaced at least 0.5 meter form said shield.

12. A surgical navigation system comprising:
    a transmitter assembly with at least one transmitter element capable of emitting electromagnetic energy, each said transmitter element, when emitting electromagnetic energy, being considered a real dipole;
    a correction sensor assembly with at least one sensor element capable of sensing electromagnetic energy is provided, wherein, relative to said transmitter assembly, said correction sensor assembly is at a fixed position and orientation so as to form a transmitter-correction sensor assembly;
    a tracker sensor assembly with at least one sensor element capable of sensing electromagnetic energy, wherein one of said transmitter-correction sensor assembly or said tracker sensor assembly is moveable relative to the other of said tracker sensor assembly or said transmitter-correction sensor assembly and one of said transmitter-correction sensor assembly or said tracker sensor assembly is part of a tracker attached to a surgical tool or to a marker attached to a patient;
    a shield formed of magnetically permeable material that is positioned so that the patient, said transmitter-correction sensor assembly and said tracker sensor assembly are located on one side of said shield, the patient is located close to said shield, said tracker sensor assembly is located further from said shield than the distance the patient is located from said shield and said transmitter-correction sensor assembly is located further from said shield than the distance said tracker sensor assembly is located from said shield and both said transmitter-correction sensor assembly and said tracker sensor assembly are moveable relative to said shield said; and a processor connected to said tracker sensor assembly to receive at least one measurement of electromagnetic field strength from said at least one tracker sensor assembly sensor element and to said correction sensor assembly to receive at least one measurement of electromagnetic field strength from said at least one correction sensor assembly sensor element and said processor being configured to:
- based on the at least one measurement of electromagnetic field strength from said at least one correction sensor assembly sensor element, determine the location of at least one virtual dipole, the at least one virtual dipole being located on the side of shield opposite the side on which said transmitter-correction sensor assembly is located;
- based on the location of the at least one real dipole, the location of the at least one virtual dipole and the at least one measurement of electromagnetic field strength of the at least one tracker sensor assembly sensor element, determine the position and orientation of said tracker sensor assembly relative to said transmitter assembly.

13. The surgical navigation system of claim 12, wherein: said processor contains data indicating:
- the location of said correction sensor assembly relative to said transmitter assembly; and
- at least one reference measurement of electromagnetic field strength made by said at least one correction sensor assembly sensor element of electromagnetic energy emitted by said transmitted assembly at least one transmitter assembly when said shield is not present; and said processor is further configured to, based on the location of said correction sensor assembly relative to said transmitter sensor assembly, the at least one reference measurement of magnetic strength made by said at least one correction sensor assembly sensor element and the at least one measurement of electromagnetic field strength made by said at least one correction sensor assembly sensor element when said shield is present, determine the location of the at least one virtual dipole.

14. The surgical navigation system of claim 12, wherein said transmitter-correction sensor assembly is spaced at least 0.5 meters from said shield.

15. The surgical navigation system of claim 12, wherein said transmitter assembly includes a plurality of transmitters.

16. The surgical navigation system of claim 12, wherein said tracker sensor assembly includes a plurality of sensor elements.

17. The surgical navigation system of claim 12, wherein said correction sensor assembly includes a plurality of sensor elements.

18. The surgical navigation system of claim 1, wherein said transmitter-correction sensor assembly is located 0.5 meter from said shield.

* * * * *